(12) United States Patent
Lee et al.

(10) Patent No.: US 9,999,649 B2
(45) Date of Patent: Jun. 19, 2018

(54) PEPTIDE HAVING ABILITY TO SYNTHESIZE COLLAGEN AND USE THEREOF

(71) Applicant: NOVACELL TECHNOLOGY INC., Pohang-si, Gyeongsangbuk-do (KR)

(72) Inventors: Tae Hoon Lee, Seoul (KR); Jae Yoon Kim, Pohang-si (KR); Jong Hyuk Yoon, Pohang-si (KR); Beom Joon Kim, Seoul (KR)

(73) Assignee: NOVACELL TECHNOLOGY INC., Pohang-si, Gyeongsangbuk-Do (KR)

( * ) Notice: Subject to any disclaimer, the term of this patent is extended or adjusted under 35 U.S.C. 154(b) by 0 days. days.

(21) Appl. No.: 14/793,178

(22) Filed: Jul. 7, 2015

(65) Prior Publication Data
US 2016/0184385 A1    Jun. 30, 2016

Related U.S. Application Data

(63) Continuation-in-part of application No. PCT/KR2013/000122, filed on Jan. 8, 2013.

(51) Int. Cl.
*A61K 8/64* (2006.01)
*A61K 38/08* (2006.01)
(Continued)

(52) U.S. Cl.
CPC ............. *A61K 38/08* (2013.01); *A61K 8/345* (2013.01); *A61K 8/64* (2013.01); *A61K 8/8147* (2013.01); *A61K 8/86* (2013.01); *A61K 8/927* (2013.01); *A61K 31/20* (2013.01); *A61K 47/542* (2017.08); *A61L 27/12* (2013.01); *A61L 27/26* (2013.01); *A61L 27/54* (2013.01); *A61Q 19/08* (2013.01); *C07K 7/06* (2013.01); (Continued)

(58) Field of Classification Search
CPC .... A61K 8/64; A61K 38/08; A61K 47/48038; A61K 47/542; C07K 7/06
See application file for complete search history.

(56) References Cited

U.S. PATENT DOCUMENTS 5,668,119 A * 9/1997 Medenica ............ A61K 31/715
514/56
8,691,195 B2 * 4/2014 Chung ................. C07K 14/495
424/62
(Continued)

FOREIGN PATENT DOCUMENTS

CN     101906140 A  * 12/2010
JP     2004049921 A    2/2004
(Continued)

OTHER PUBLICATIONS

Yoon et al., Biochem. & Biophys. Res. Comm., 2012, 428(3), 1-6.*
(Continued)

*Primary Examiner* — Jeffrey E. Russel
(74) *Attorney, Agent, or Firm* — Lucas & Mercanti, LLP

(57) ABSTRACT

Provided are a cosmetic composition and pharmaceutical composition for wound healing capable of efficiently performing collagen synthesis in skin, wherein the compositions contain, as an active ingredient, YIGSR peptide having the amino acid sequence of SEQ ID NO: 1 or a peptide derivative having a palmitoyl group added to an N-terminal of the peptide.

1 Claim, 11 Drawing Sheets

(51) Int. Cl.
    *A61K 47/54*     (2017.01)
    *A61Q 19/08*     (2006.01)
    *C07K 7/06*     (2006.01)
    *A61K 8/34*     (2006.01)
    *A61K 8/81*     (2006.01)
    *A61K 8/86*     (2006.01)
    *A61K 8/92*     (2006.01)
    *A61K 31/20*     (2006.01)
    *A61L 27/12*     (2006.01)
    *A61L 27/26*     (2006.01)
    *A61L 27/54*     (2006.01)

(52) U.S. Cl.
    CPC .... *A61K 2800/596* (2013.01); *A61K 2800/74* (2013.01); *A61L 2300/204* (2013.01); *A61L 2300/402* (2013.01)

(56) References Cited

U.S. PATENT DOCUMENTS

| | | | |
|---|---|---|---|
| 2005/0063937 | A1 | 3/2005 | Li et al. |
| 2005/0272662 | A1* | 12/2005 | Stupp .................. A61K 9/1075 514/8.3 |
| 2006/0067909 | A1 | 3/2006 | West et al. |
| 2006/0247165 | A1* | 11/2006 | Stupp .................. A61K 38/08 424/85.2 |
| 2011/0129531 | A1 | 6/2011 | Collette et al. |
| 2015/0352168 | A1* | 12/2015 | Yan .................. A61K 9/1652 424/547 |

FOREIGN PATENT DOCUMENTS

| | | | |
|---|---|---|---|
| KR | 10-2009-0133068 A | | 12/2009 |
| KR | 2013055505 A | * | 5/2013 |

OTHER PUBLICATIONS

Kawada et al. Evaluation of anti-wrinkle effects of a novel cosmetic containing niacinamide. Journal of Dermatology. 2008, vol. 35, pp. 637-642.*

J.H. Yoon, et al; Laminin peptide YIGSR induces collagen synthesis in . . . ; Biochemical and biophysical research communications; vol. 428; No. 3; Oct. 2012; pp. 416-421 (6 pages).

F. Li, et al; Cellular and nerve regeneration within a biosynthetic extracellular matrix . . . ; Proceeding of the National Academy of Sciences of the USA; vol. 100; No. 26; Dec. 2003; pp. 15346-15351.

International Search Report dated Aug. 20, 2013 for PCT/KR2013/000122.

Zhang et al., "Coverting Peptides into Drug Leads by Lipidation", Curr. Med. Chem., 2012, vol. 19, No. 11, pp. 1-18.

* cited by examiner

YIGSR(24h)

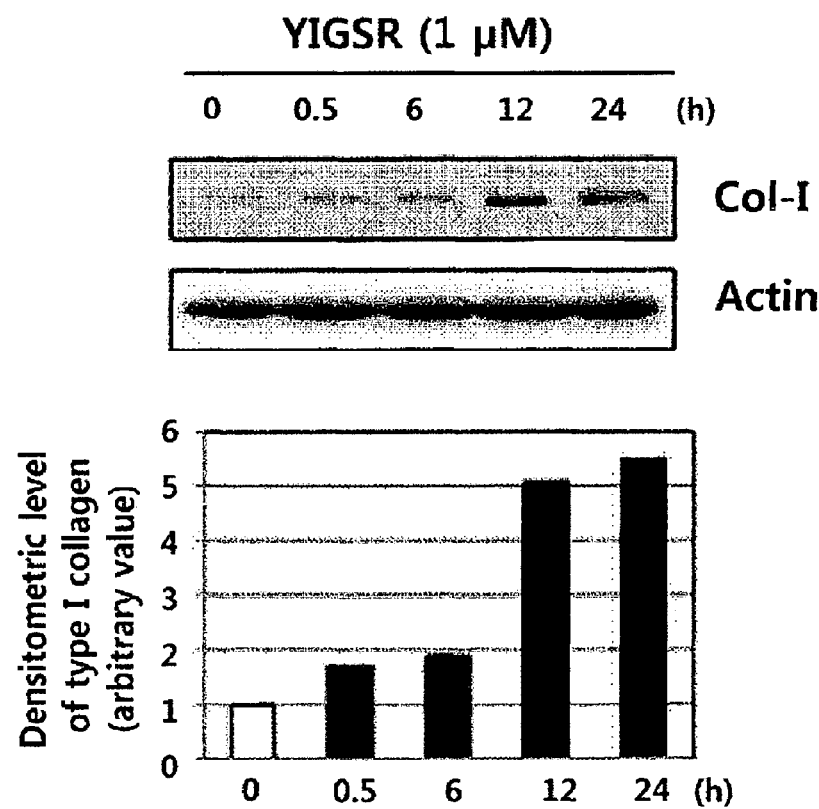

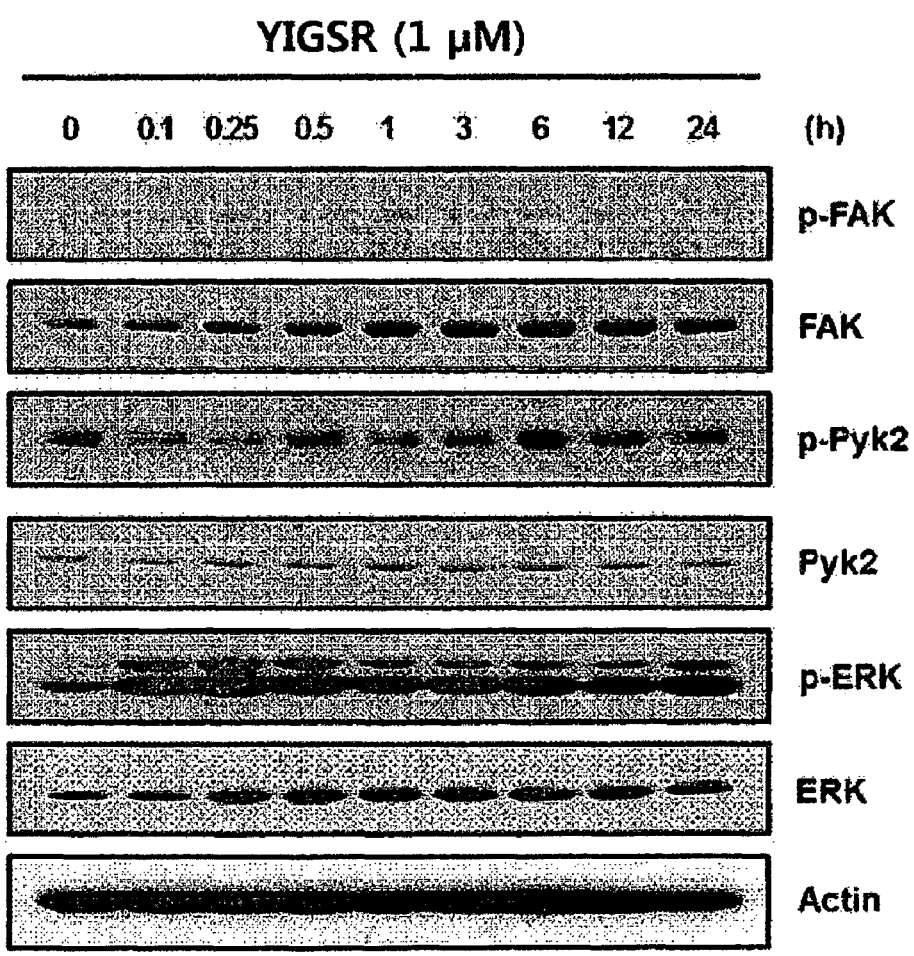

Dose dependency

Pal-YIGSR (µM)

Time dependency

Pal-YIGSR (100 µM)

PEPTIDE HAVING ABILITY TO SYNTHESIZE COLLAGEN AND USE THEREOF

CROSS REFERENCE TO RELATED APPLICATION

This application is a continuation in part of PCT/KR2013/000122, filed Jan. 8, 2013, the content of which is incorporated herein by reference.

FIELD OF THE INVENTION

The present disclosure relates to a peptide and use thereof, and more particularly to a novel peptide having an ability to synthesize collagen and use thereof.

BACKGROUND OF THE INVENTION

As human getting older, skin aging appears. A wrinkle is one of a representative symptom of skin aging. A representative cause of wrinkle generation, which is a phenomenon representing age, is resulted from degradation of collagen which forms a matrix in the skin dermis. Production of collagen in skin is declined as aging proceeded.

Typical materials, which are known to facilitate collagen synthesis, include retinoid (RE36068), transforming growth factor-β (TGF-β), betulinic acid (JP8-208424), and wild Chinese yam (*Dioscorea japonica*) extract (Korean Patent Publication no. 2009-0055079) etc.

However, the typical collagen synthesis-enhancing agent has drawbacks such as low efficiency, high costs for a recombinant protein and low reproducibility in case of a natural extract.

The present invention is created in order to resolve various limitations including drawbacks described above, thus the purpose of the present invention is provide a novel peptide and use thereof, wherein the peptide can be used as a cosmetic composition for alleviating skin aging or wrinkle or as an agent for wound healing by effectively enhancing collagen synthesis with a relatively low cost. However, these purposes are illustrative, and the scope of the present invention is not limited thereto.

SUMMARY OF INVENTION

In an aspect of the present invention, provided is a palmitoylated peptide in which a palmitoyl group is added to an N-terminal of a YIGSR peptide consisting of the amino acid sequence of SEQ ID: 1.

In another aspect of the present invention, provided is a composition comprising the palmitoylated peptide.

In another aspect of the present invention, provided is a composition for alleviating skin aging comprising YIGSR peptide having the amino acid sequence of SEQ ID NO: 1 as an active ingredient.

In another aspect of the present invention, provided is a cosmetic composition for alleviating wrinkle including, as an active ingredient, a peptide having the amino acid sequence of SEQ ID NO: 1 (YIGSR), or a palmitoylated peptide in which a palmitoyl group is added to an N-terminal of a YIGSR peptide consisting of the amino acid sequence of SEQ ID: 1.

In accordance with yet another aspect of the present invention, provided is an pharmaceutical composition for wound healing containing YIGSR peptide having the amino acid sequence of SEQ ID NO: 1, or a palmitoylated peptide in which a palmitoyl group is added to an N-terminal of a YIGSR peptide consisting of the amino acid sequence of SEQ ID: 1.

In accordance with still another aspect of the present invention, provided is a dermal filler containing YIGSR peptide having the amino acid sequence of SEQ ID NO: 1, or a peptide derivative having a palmitoyl group added to an N-terminal of the peptide as an active ingredient.

In accordance with yet still another aspect of the present invention, provided is a method for wound healing comprising: administering a pharmaceutically effective amount of YIGSR peptide having the amino acid sequence of SEQ ID NO: 1 or a palmitoylated peptide in which a palmitoyl group is added to an N-terminal of a YIGSR peptide consisting of the amino acid sequence of SEQ ID: 1 to a subject having a wound.

In accordance with a yet further aspect of the present invention, provided is a use of YIGSR peptide having the amino acid sequence of SEQ ID NO: 1, or a peptide derivative having a palmitoyl group added to an N-terminal of the peptide to be used in preparation of a cosmetic composition for alleviating wrinkle.

In an aspect of the present invention, provided is a cosmetic composition comprising: YIGSR peptide consisting of the amino acid sequence of SEQ ID NO: 1 or the palmitoylated peptide of claim 1, and at least one additional component selected from the group consisting of ferulic acid, niacinamide and allantoin.

In an aspect of the present invention, provided is a method of alleviating wrinkle of a subject comprising: administering a pharmaceutically effective amount of YIGSR peptide consisting of the amino acid sequence of SEQ ID NO: 1 or the palmitoylated peptide of claim 1 dermally to the subject.

In an aspect of the present invention, provided is a wound healing composition comprising: YIGSR peptide consisting of the amino acid sequence of SEQ ID NO: 1 or the palmitoylated peptide of claim 1, and at least one additional component selected from the group consisting of carnosine, *Centella asiatica* extract, madecassoside and madecassic acid.

In an aspect of the present invention, provided is a dermal filler composition comprising: YIGSR peptide consisting of the amino acid sequence of SEQ ID NO: 1 or the palmitoylated peptide of claim 1, and at least one polymer selected from the group consisting of hyaluronic acid, collagen, a biosynthetic polymer.

According to an embodiment of the present invention as described above, a novel peptide having an ability to synthesize collagen is provided. Therefore, the scope of the present invention is not limited by these effects.

BRIEF DESCRIPTION OF THE DRAWINGS

FIGS. 1a, 1b, and 1c show a result of evaluating a change in collagen expression by YIGSR peptide (SEQ ID NO: 1) treatment according to one embodiment of the present invention in Hs27 cells through western blot analysis and real time RT-PCR analysis. FIG. 1a is a graph showing a change in collagen I protein expression depending on concentrations of treated YIGSR peptide (SEQ ID NO: 1) (0, $10^{-2}$, $10^{-1}$, 1, 10, $10^2$, $10^3$, $10^4$, and $10^5$ nM). FIG. 1b is a graph showing a change in collagen I protein expression depending on a period of time of YIGSR peptide (SEQ ID NO: 1) ($10^3$ nM) treatment (0, 0.5, 6, 12, and 24 hours). FIG. 1c is a graph showing a change in collagen I mRNA expression depending on concentrations of treated YIGSR peptide (SEQ ID NO: 1) (0, $10^{-2}$, $10^{-1}$, 1, 10, $10^2$, $10^3$, $10^4$, and $10^5$ nM).

FIG. 2a is a graph showing cell viability of Hs27 cells depending on a change in concentrations of treated YIGSR peptide (SEQ ID NO: 1) (0, 10, $10^2$, $10^3$, $10^4$, and $10^5$ nM), and FIG. 2b is a graph showing Hs27 cell viability depending on a period of time of YIGSR peptide (SEQ ID NO: 1) ($10^3$ nM) treatment (0, 0.1, 0.25, 0.5, 1, 3, 6, 12, and 24 hours).

FIGS. 4a and 4b show results of evaluating phosphorylation levels of FAK, Pyk2, and ERK, which are downstream signal of a laminin receptor, in order to identify a signaling mechanism involved in increased collagen expression induced by YIGSR peptide (SEQ ID NO: 1) according to one embodiment of the present invention by using western blot analysis. FIG. 4a is a western-blot image, and FIG. 4b is a graph obtained by densitometrically analyzing the western blot image.

FIG. 5a shows a result of PF573228 treatment, and FIG. 5b shows a result of PD98059 treatment, wherein the PF573228 is an FAK inhibitor and the PD98059 is an ERK inhibitor.

FIG. 6a is Dose dependency and FIG. 6b is Time dependency.

DETAILED DESCRIPTION OF THE INVENTION

Figure 1A:
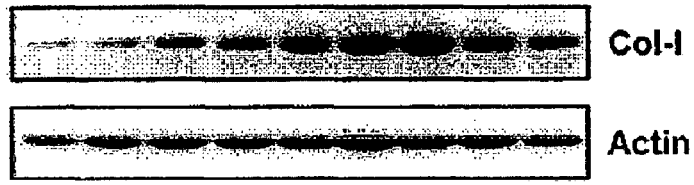
Figure 1A:
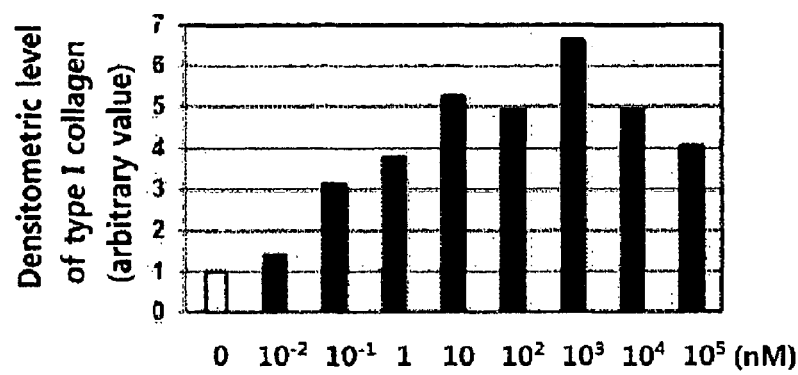

Hereinafter, the present invention will be described in more detail.

In an aspect of the present invention, provided is a palmitoylated peptide in which a palmitoyl group is added to an N-terminal of a YIGSR peptide consisting of the amino acid sequence of SEQ ID: 1.

In another aspect of the present invention, provided is a composition comprising the palmitoylated peptide.

The composition may be a pharmaceutical composition, a cosmetic composition or a dermal filler composition.

In another aspect of the present invention, provided is a composition for alleviating skin aging comprising YIGSR peptide consisting of the amino acid sequence of SEQ ID NO: 1 or the palmitoylated peptide of as an active ingredient.

YIGSR peptide having the amino acid sequence of SEQ ID NO: 1 according to one embodiment of the present invention regulates collagen expression in a transcription level, and provides an effect of increasing collagen I production in a treatment dose and time-dependent manner. The YIGSR peptide expressed by SEQ ID NO: 1 significantly increases collagen I production in a low concentration of $10^3$ to $10^4$ nM, and the Pal-YIGSR (Pal-SEQ ID NO: 1), which is a derivative of the peptide, provides an effect of significantly increasing collagen I production in a high concentration of 50 to 100 µM. The effect of increasing collagen production is not triggered by inhibition of MMP-1 hydrolase expression, which degrades collagen, but triggered by phosphorylation of FAK, Pyk2 and ERK which are downstream signal transduction mechanisms of a laminin receptor. Thus, the composition may be used to alleviate skin aging facilitated by a decreased collagen I content. Further, the palmitoylated YIGSR peptide (Pal-SEQ ID NO: 1) showed more potent effect than the YIGSR peptide whereas oleylated YIGSR peptide (oleylated-SEQ ID NO: 1) showed no improved activity compared to original YIGSR peptide (SEQ ID NO: 1).

In another aspect of the present invention, provided is a cosmetic composition for alleviating wrinkle including, as an active ingredient, a YIGSR peptide consisting of the amino acid sequence of SEQ ID NO: 1, or a palmitoylated peptide in which a palmitoyl group is added to an N-terminal of a YIGSR peptide consisting of the amino acid sequence of SEQ ID: 1.

When the peptide according to one embodiment of the present invention is used in a cosmetic composition, a formulation of the composition is not specifically limited. For example, the composition may be a cosmetic composition having a formulation of toner, nourishing softener, massage cream, nourishing cream, pack, gel, or skin adhering-type cosmetic, and the composition may have a formulation for dermal administration such as lotion, ointment, gel, cream, patch, or spray.

The composition of the present invention may further include an appropriate carrier, excipient, and diluent typically used in preparation of a cosmetic. The carrier, excipient, and diluent may be appropriately selected based on a formulation of the cosmetic, and include hydrocarbons such as Vaseline, liquid paraffin, gelated hydrocarbon (a.k.a.: plastibase); animal and vegetable oils such as heavy chain fatty acid triglyceride, pig fat, hard fat, and cacao oil; high fatty acid alcohol and fatty acid and esters thereof such as cetanol, stearyl alcohol, stearic acid, and palmitic acid isopropyl; aqueous base material such as macrogol (polyethylene glycol), 1,3-butylene glycol, glycerol, gelatin, white sugar, and sugar alcohol; emulsifier such as glycerin fatty acid ester, stearic acid polyoxyl, and polyoxyethylene hardened castor oil; adhesive such as acrylic acid ester, and sodium alginate; propellants such as liquefied petroleum gas, and carbon dioxide; and preservant such as paraoxybenzoic acid ester.

In addition, the cosmetic composition may comprise any additional components such as a whitening agent, an antioxidant agent, an additional wound healing agent. The whitening agent may be niacinamide, arbutin, licorice extract, resveratrol bearberry extract, vitamin A, vitamin C or Kojic acid. The antioxidant agent may be vitamin E, coenzyme Q10, idebenone, lycopene, vitamin C, silymarin, resveratrol, genistein, pycogenol, pomegranate, niacinamide, grapes seed extract, or coffeeberry extract. The additional wound healing agent may be epidermal growth factor (EGF), transforming growth factor-α (TGF-α), transforming growth factor-β (TGF-β), hepatocyte growth factor (HGF), vascular endothelial growth factor (VEGF), platelet-derived growth factor (PDGF), fibroblast growth factor-1 (FGF-1), fibroblast growth factor-2 (FGF-2), keratinocyte growth factor (KGF), niacinamide, allantoin, acrnosine, *Celtella asiatica* extract, madecassoside, or madecassic acid.

Thus, in a preferred embodiment of the present invention, the provided is a cosmetic composition comprising: a YIGSR peptide consisting of the amino acid sequence of SEQ ID NO: 1, or a palmitoylated peptide in which a palmitoyl group is added to an N-terminal of the YIGSR peptide (Pal-SEQ ID NO: 1), and at least one additional component selected from the group consisting of ferulic acid, niacinamide and allantoin.

In accordance with yet another aspect of the present invention, provided is an pharmaceutical composition for wound healing containing YIGSR peptide having the amino acid sequence of SEQ ID NO: 1, or a palmitoylated peptide in which a palmitoyl group is added to an N-terminal of a YIGSR peptide consisting of the amino acid sequence of SEQ ID: 1.

The pharmaceutical composition may comprises at least one additional wound healing agent or soothing agent. The additional wound healing agent may be epidermal growth factor (EGF), transforming growth factor-α (TGF-α), transforming growth factor-β (TGF-β), hepatocyte growth factor (HGF), vascular endothelial growth factor (VEGF), platelet-derived growth factor (PDGF), fibroblast growth factor-1 (FGF-1), fibroblast growth factor-2 (FGF-2), keratinocyte growth factor (KGF), niacinamide, allantoin, acrnosine, *Celtella asiatica* extract, madecassoside, or madecassic acid. The soothing agent may be lidocaine, chia seed extract, *Rosa centifolia* flower extract.

In a preferred embodiment of the present invention, the provided is a wound healing composition comprising: YIGSR peptide consisting of the amino acid sequence of SEQ ID NO: 1 or a palmitoylated peptide in which a palmitoyl group is added to an N-terminal of the YIGSR peptide (SEQ ID NO: 1), and at least one additional component selected from the group consisting of carnosine, *Centella asiatica* extract, madecassoside and madecassic acid.

In accordance with still another aspect of the present invention, provided is a dermal filler containing YIGSR peptide consisting of the amino acid sequence of SEQ ID NO: 1, or a palmitoylated peptide in which a palmitoyl group is added to an N-terminal of the YIGSR peptide (Pal-SEQ ID NO: 1) as an active ingredient.

The dermal filler composition may comprise any additional component suitable for the preparation of dermal filler. Such component may be filling agents such as hyaluronic acid, collagen, or a synthetic polymer and the synthetic polymer may be calcium hydroxylapatite, polymethylmethacrylate and poly-L-lactic acid.

In accordance with yet still another aspect of the present invention, provided is a method for wound healing comprising: administering a pharmaceutically effective amount of YIGSR peptide having the amino acid sequence of SEQ ID NO: 1 or a palmitoylated peptide in which a palmitoyl group is added to an N-terminal of a YIGSR peptide consisting of the amino acid sequence of SEQ ID: 1 to a subject having a wound.

In accordance with a yet further aspect of the present invention, provided is a use of YIGSR peptide having the amino acid sequence of SEQ ID NO: 1, or a palmitoylated peptide in which a palmitoyl group is added to an N-terminal of the YIGSR peptide (Pal-SEQ ID NO: 1) to be used in preparation of a cosmetic composition for alleviating wrinkle.

In an aspect of the present invention, provided is a method of alleviating wrinkle of a subject comprising: administering a pharmaceutically effective amount of YIGSR peptide consisting of the amino acid sequence of SEQ ID NO: 1 or a palmitoylated peptide in which a palmitoyl group is added to an N-terminal of the YIGSR peptide (Pal-SEQ ID NO: 1) dermally to the subject.

YIGSR peptide having the amino acid sequence of SEQ ID NO: 1 provides an effect of significantly increasing collagen I production in a low concentration of $10^3$ to $10^4$ nm.

Initially, YIGSR peptide (SEQ ID NO: 1), which is a well preserved region of collagen-binding protein such as laminin, is known as a collagen-binding motif. It has been documented that the YIGSR peptide (SEQ ID NO: 1) inhibits growth of leukemia cells (see Yoshida et al., (1999) *Br. J. Cancer,* 80(12): 1898-1904) and thus has potency as an anticancer agent (see Graf et al., (1987) *Cell,* 48: 989-996). However, a collagen-synthesizing ability of the YIGSR peptide has not documented. Thus, the present inventors tried to find a peptide which enhances collagen-synthesizing ability, and, as a result, have completed the present invention by demonstrating that YIGSR peptide (SEQ ID NO: 1) and a palmitoylated derivatized form of YIGSR peptide (Pal-SEQ ID NO: 1) show enhanced collagen synthesis.

In the composition of the present invention, an effective amount of YIGSR peptide (SEQ ID NO: 1) may be varied depending on types of diseased region of a patient, an application region, a treatment number, a period of treatment time, a formulation, a state of patient, and types of adjuvant. An amount of use may be 0.01 µg/kg/day to 10 mg/kg/day without specific limitation. The one day dose may be administered once a day, or dividedly administered in 2 to 3 portions in a day with an appropriate interval. Also, the one day dose may be intermittently administered with several days of interval.

The composition of the present invention may contain YIGSR peptide having the amino acid sequence of SEQ ID NO: 1 and a peptide derivative having a palmitoyl group added to an N-terminal of the peptide in 0.1 to 100 wt % based on the total weight of the composition.

The composition of the present invention may further include an appropriate carrier, excipient, and diluent typically used in preparation of a pharmaceutical composition. Also, a solid or liquid additive for formulation may be used to prepare the pharmaceutical composition. The additive for formulation may either be organic or inorganic.

The acceptable carrier in the pharmaceutical codex may be varied depending on a formulation, but include hydrocarbons such as Vaseline, liquid paraffin, gelated hydrocarbon (a.k.a.: plastibase); animal and vegetable oils such as heavy chain fatty acid triglyceride, pig fat, hard fat, and cacao oil; high fatty acid alcohol and fatty acid and esters thereof such as cetanol, stearyl alcohol, stearic acid, and palmitic acid isopropyl; aqueous base material such as macrogol (polyethylene glycol), 1,3-butylene glycol, glycerol, gelatin, white sugar, and sugar alcohol; emulsifier such as glycerin fatty acid ester, stearic acid polyoxyl, and polyoxyethylene hardened castor oil; adhesive such as acrylic acid ester, and sodium alginate; propellants such as liquefied petroleum gas, and carbon dioxide; and preservant such as paraoxybenzoic acid ester. The topical agent of the present invention may be prepared through a typical method by using the carrier described above. In addition to the carrier described above, it is possible to combine a stabilizer, flavoring agent, coloring agent, pH-adjusting agent, diluent, surfactant, preservant, and antioxidant, etc. as necessary. The topical agent of the present invention may be applied on topical wound by a typical method.

The excipient may include, for example, lactose, sucrose, white sugar, glucose, corn starch, starch, talc, sorbite, crystalline cellulose, dextrin, kaolin, calcium carbonate, and silicon dioxide, etc. A binding agent may include, for example, polyvinyl alcohol, polyvinyl ether, ethyl cellulose, methyl cellulose, gum arabic, tragacanth, gelatin, shellac, hydroxypropyl cellulose, hydroxypropylmethyl cellulose, calcium citrate, dextrin, and pectin, etc. A lubricant may include, for example, magnesium stearate, talc, polyethylene glycol, silica, and hardened vegetable oil, etc. As a coloring agent, all materials, which are typically permitted to be added in medicinal products, may be used. A tablet and granule may be appropriately coated with sugar coating, gelatin coating, and others as necessary. Also, a preservant and antioxidant may be added as necessary.

The pharmaceutical composition of the present invention may be prepared in any formulation typically prepared in the art (see document [Remington's Pharmaceutical Science, the newest edition; Mack Publishing Company, Easton Pa.]). A form of the formulation is not specifically limited, but may preferably be a topical agent. The topical agent of the present invention may include a typical form of topical agent such as sheet, a liquid spray, spray, lotion, cream, cataplasma, dust, penetration pad, gel including hydrogel, paste, liniment, ointment, aerosol, powder, suspension, and transdermal absorbent. These formulations are disclosed in the document [Remington's Pharmaceutical Science, 15th Edition, 1975, Mack Publishing Company, Easton, Pa. 18042 (Chapter 87: Blaug, Seymour) which is generally known formulary in all pharmaceutical chemistry.

As an example of the present invention, the composition may be directly applied on skin or wound region. Namely, the composition may be distributed on a wound region. The sheet form is applied on a wound region while appropriate dressing is performed on the applied region to protect the wound and to prevent a therapeutic effect of an active ingredient from decline. Any commercially available or typically known dressing may be used. Examples of commercially available dressing may include Compeel, Duoderm, Tagaderm and Opsite. In addition, it is possible to combine a stabilizer, flavoring agent, coloring agent, pH-adjusting agent, diluent, surfactant, preservant, and antioxidant, etc. as necessary.

Further, the pharmaceutical composition according to the present invention may be adhered to a solid support such as a wound peeling cover of a typical sticking plaster and then used. As an aspect of the present invention, a solid support is firstly coated with an adhesive layer to enhance adherence of a peptide derivative to the solid support. Examples of the adhesive may include polyacrylate and cyanoacrylate.

Many of formulations in such form are commercially available, and examples of the formulation may include the sticking plaster having non-adhesive wound peeling cover in a penetrated plastic film form (Smith & Nephew Ltd.), BAND-AID from Johnson & Johnson, in a form of thin strip, patch, spot, or flexible strip, Curity CURAD Ouchless sticking plaster from Colgate-Palmolive Co. (Kendall), and STIK-TITE elastic strip from American WhiteCross Laboratories, Inc.

As an example of the present invention, the composition according to the present invention may be formulated in a liquid spray form including a mixture of the peptide derivative and physiological saline at a certain volume ratio. As an example of the present invention, the pharmaceutical composition according to the present invention may be formulated in an ointment form by mixing the peptide derivative of the present invention and aqueous ointment base material and adding physiological saline to the mixture.

However, the amount of use of the pharmaceutical composition of the present invention may be determined by various factors such as an administration route, age, sex, and body weight of a patient, severity of a patient, a type of wound, application region, treatment number, period of treatment time, formulation, state of a patient, and types of adjuvant, and thus it should be understood that the effective amount does not limit the scope of the present invention in any aspect.

In accordance with another aspect of the present invention, provided is a dermal filler including, as an active ingredient, YIGSR peptide having the amino acid sequence of SEQ ID NO: 1.

The wording "dermal filler" or "filler" means a material, which is an ingredient similar to skin tissue, to be inserted into a particular region to expand soft tissue thereby being used in wrinkle alleviation or contouring. For soft tissue expansion, collagen is often used as an injectable material. Also, numerous other materials have been used as an injectable dermal filler including a protein, lipid, hyaluronic acid (HA), polyalcohol and other polymers such as carboxymethyl cellulose, and dextran. As a dermal feller including collagen as a main ingredient, materials as below have been known: EVOLENCE 30 (brand name of dermal filler of ColBar LifeScience Co.) including pig collagen as a main ingredient, Zyderm or Zyplast (brand name of dermal filler of Inamed Co.) including bovine collagen as a main ingredient, CosmoDerm or CosmoPlast (brand name of dermal filler of Inamed Co.) including human collagen as a main ingredient. A dermal filler including hyaluronic acid as a main ingredient includes Rofilan (brand name of dermal filler of Rofil/Philoderm Co.), Perlane and Restylane (brand names of dermal filler of Medicis/Q-Med AB Co.), Teosyal (brand name of dermal filler of Teoxane SA Co.), and Surgiderm (brand name of dermal filler of Corneal Laboratoire Co.). The dermal filler according to one aspect of the present invention may be prepared by loading a suitable amount of the peptide according to one embodiment of the present invention on the known dermal filler or binding the peptide to a polymer, which becomes a backbone of the dermal filler, through covalent or non-covalent binding.

In accordance with another aspect of the present invention, provided is a method for wound healing, the method including administering pharmaceutically effective amount of YIGSR peptide having the amino acid sequence of SEQ ID NO: 1 to a subject having a wound.

The subject having a wound may be mammals except human beings.

In accordance with another aspect of the present invention, provided is YIGSR peptide having the amino acid sequence of SEQ ID NO: 1 to be used in wound healing.

In accordance with another aspect of the present invention, provided is a use of YIGSR peptide having the amino acid sequence of SEQ ID NO: 1 to be used in preparation of a cosmetic composition for wrinkle alleviation.

EXAMPLES

Hereinafter, the present invention will be described in detail with reference to Examples, Experimental Examples and Preparation Examples. However, the present invention is not limited to the Examples, Experimental Examples, and Preparation Example disclosed hereinafter, and can be achieved in various embodiments different from one another. Examples, Experimental Examples, and Preparation Example hereinafter complete the disclosure of the present invention, and are provided to completely notify a scope of the present invention to a person skilled in the art.

Example 1: Preparation of YIGSR

YIGSR peptide (SEQ ID NO: 1) was prepared by requesting a peptide preparation company (Anygen, Korea) for preparation.

Example 2: Preparation of Palmitoyl-YIGSR

Prepared was a peptide derivative, in which a palmitoyl group is attached to an N-terminal of the YIGSR peptide (SEQ ID NO: 1) of example 1 (Pal-YIGSR, molecular weight: 846) (Pal-SEQ ID NO: 1) through the same method as in Example 1 by using palmitoyl-tyrosine instead of tyrosine (Anygen, Korea).

Comparative Example 1: Preparation of Pal-RGD

RGD peptide having an N-terminal, to which a palmitoyl group is attached, was prepared through the same method as in Example 1 by using palmitoyl-arginine. RGD, a peptide having an integrin-binding activity, is a material used as a cell-adhesion agent, etc.

Comparative Example 2: Preparation of Oleyl-YIGSR

YIGSR peptide (SEQ ID NO: 1) having an N-terminal, to which an oleyl group is added instead of the palmitoyl group, was prepared through the same method as in Example 1 by using oleyl-tyrosine instead of tyrosine.

Example 3: Culture of Hs27 Cells

Hs27 cells (ATCC), which are human skin fibroblasts, were cultured by using DMEM medium (Lonza, USA), to which 10% FBS was added (Lonza, USA), under the condition of 95% of humidity, 5% $CO_2$, and 37° C. For the Hs27 cells, cells subcultured between passages 5 to 20 were used. Prior to peptide treatment, cells were cultured in FBS-free DMEM medium for 24 hours, and then treated.

Experimental Example 1: Analysis of Change in Collagen I Expression by YIGSR Peptide 1-1: Analysis of Change in Collagen I Expression by YIGSR Peptide Through Western Blot To evaluate an influence of YIGSR peptide (SEQ ID NO: 1) according to one embodiment of the present invention on skin fibroblasts, firstly, Hs27 cells were treated with each concentration of the peptide of Example 1, and an expression level of type I collagen protein was evaluated through western blot analysis.

Hs27 skin fibroblasts of Example 3 were treated with each concentration of the peptide (0, $10^{-2}$, $10^{-1}$, 1, 10, $10^2$, $10^3$, $10^4$, and $10^5$ nM) for 24 hours. Then, the treated cells were sonicated in the lysis buffer (150 mM NaCl, 1% Triton X-100, 10 mM Tris, mM EDTA, pH 7.4). Thereafter, supernatant was isolated through centrifugation, and quantification was performed through Bradford assay. The same amount of a protein was mixed in a 5× sample buffer, and the mixture was heated for 5 minutes at 95° C. The resultant was electrophoresed on 6-15% concentration gradient SDS-polyacrylamide gel electrophoresis (SDS-PAGE), and then adsorbed to a nitrocellulose membrane. An anti-type I collagen primary antibody (Rockland, USA) and anti-actin primary antibody (Santa Cruz, USA) were diluted in TBST buffer (Tris buffered saline with 0.05% Tween 20, pH 7.6) including 5% skimmed milk and reacted for 16 hours. Then, the resultant was washed with TBST for 10 minutes 6 times. Thereafter, the membrane was treated with an anti-mouse rabbit peroxidase-conjugated secondary antibody (KPL, USA) for reaction for one hour at room temperature, and washed again with TBST 6 times for 10 minutes followed by development with the enhanced chemiluminescent (ECL) solution (Amersham, USA) for evaluation. In addition, the western blot image was quantitatively compared with densitometric analysis by using image J program (Ver 1.38, //rsbweb.nih.gov/ij/index.html).

Figure 1C:
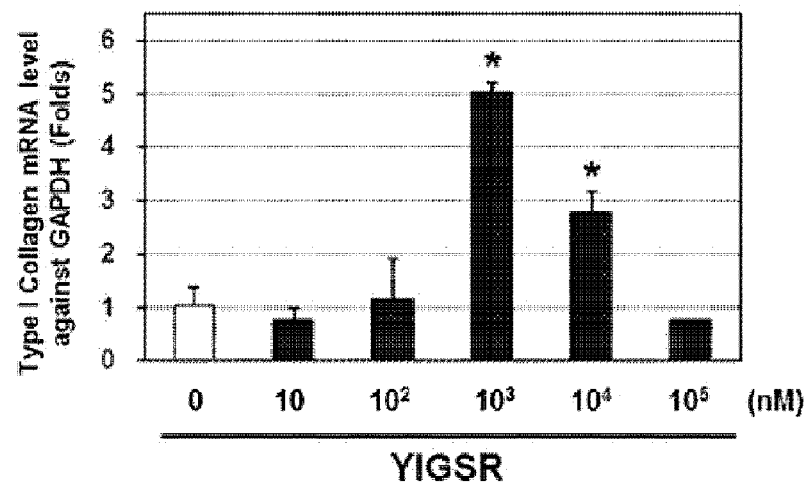

Consequently, as shown in FIGS. 1a, 1b, and 1c, for YIGSR peptide (SEQ ID NO: 1) according to one embodiment of the present invention, expression of collagen I protein was remarkably increased in a treatment does-dependent manner, and maximum collagen production was shown in YIGSR peptide (SEQ ID NO: 1) concentration of $10^3$ nM. Moreover, when comparing with an expression level of collagen I of untreated Hs27 cells, collagen I was increased by at least 6 times upon $10^3$ nM YIGSR peptide (SEQ ID NO: 1) treatment.

In sequence, the present inventors evaluated a collagen production level depending on a period of time of YIGSR peptide (SEQ ID NO: 1) treatment through western blot analysis. The Hs27 skin fibroblasts of Example 3 were treated with 1 μM YIGSR peptide (SEQ ID NO: 1) for 0, 0.5, 6, 12 and 24 hours, and then western blot was performed on the treated cells through the same method as described above. In addition, amounts of expression were quantitatively compared by using image J program (Ver 1.38, //rsbweb.nih.gov/ij/index.html) for the western blot image.

Consequently, as shown in FIG. 1b, collagen I expression in Hs27 cells was increased as a period of time of YIGSR peptide treatment was getting longer. For 24 hour-treatment, collagen I expression was increased by about 5 times with respect to that of YIGSR peptide (SEQ ID NO: 1)-untreated Hs27 cells.

1-2: Analysis of Change in Collagen I Expression by YIGSR Peptide Through Quantitative RT-PCR Then, the present inventors evaluated an influence of YIGSR peptide (SEQ ID NO: 1) on collagen I production in an mRNA level. Hs27 skin fibroblasts of Example 3 were treated with each concentration of the peptide (0, 10, $10^2$, $10^3$, $10^4$, and $10^5$ nM) for 24 hours. Then, total RNA was extracted from the treated cells by using the TRIzol reagent (Invitrogen Corp, USA). Reverse transcription PCR was performed with 1 μg of the extracted RNA by using an oligo (dT) primer and leukemia virus reverse transcriptase. Then, 8 μl of the PCR amplification product was mixed with 10 μl of the 2xSYBR Green I premix ExTaq (TAKARA, Japan), and 2 μl of a mixture of 1 μM of sense and antisense primers. Thereafter, real-time qPCR was performed by using Bio-Rad CFX96 Real-time PCR detection system. The real-time qPCR condition for amplification was as follows: heating at 95° C. for 1 minute; and 40 repetitive cycles of melting (95° C., 15 sec), annealing (60° C., 15 sec), and amplification (72° C., 30 sec). Then, a melting curve was analyzed as provided by Bio-Rad CFX96 Real-time PCR detection system. Primers used to identify collagen I mRNA were as follows:

```
Sense primer:
                                    (SEQ ID NO: 2)
5'-GAACGCGTGTCATCCCTTGT-3';
and Anti-sense primer:
                                    (SEQ ID NO: 3)
5'-GAACGAGGTAGTCTTTCAGCAACA-3'.
```

Consequently, as shown in FIG. 1c, there was a tendency similar to the expression level of collagen I protein, and the highest collagen I mRNA level was exhibited when $10^3$ nM YIGSR peptide was treated (see FIG. 1c). The result demonstrates that YIGSR peptide (SEQ ID NO: 1) according to one embodiment of the present invention regulates collagen I in a transcriptional level.

Experimental Example 2: Analysis of Change in Cell Viability by YIGSR Peptide

To evaluate an influence of YIGSR peptide (SEQ ID NO: 1) according to one embodiment of the present invention on cell viability, cell viability depending on concentration and a period of time of treatment of the peptide was evaluated through MTT analysis.

Hs27 cells of Example 3 were seeded on a 96-well plate at the ratio of 1×$10^4$ cells/well, and then cultured for 24 hours. Thereafter, cells were further cultured for 24 hours in a serum-free medium. Then, cells were treated with YIGSR peptide (SEQ ID NO: 1) of example 1 in concentrations of 0, 10, $10^2$, $10^3$, $10^4$ and $10^5$ nM, and cultured for 24 hours. Thereafter, a medium was removed, and 0.5 mg/ml MTT (Sigma-Aldrichi, USA) dissolved in PBS was added. The resultant was reacted in $CO_2$ cell incubator at 37° C. for 3 hours. Then, the MTT solution was removed and 100 μl DMSO solution was added to each well. The plate was vortexed for 10 minutes, and absorbance of the solution was measured at 540 nm.

Figure 2A:
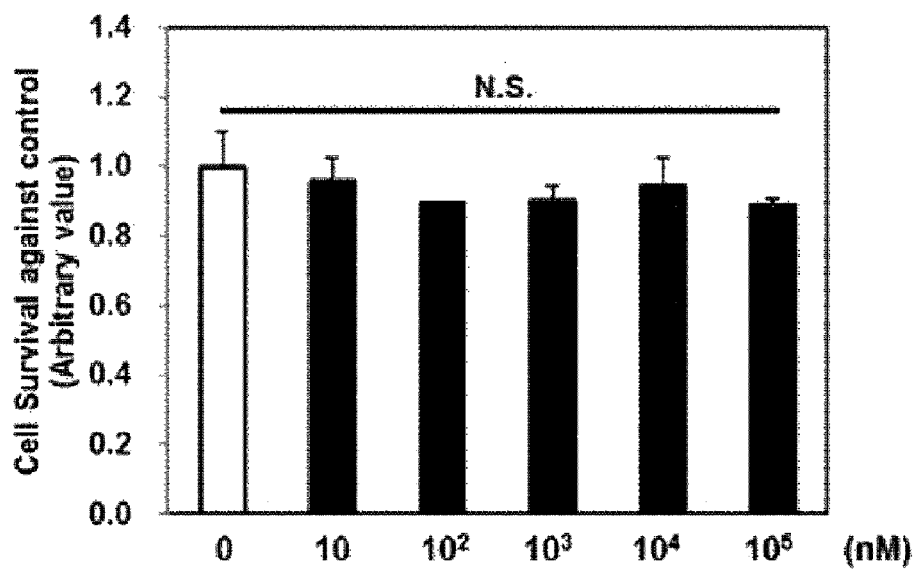
FIGS. 2a and 2b show results of evaluating a change in cell viability by YIGSR peptide (SEQ ID NO: 1) treatment according to one embodiment of the present invention through MTT analysis.

Consequently, as shown in FIG. 2a, when comparing with the control which is not treated with YIGSR peptide (SEQ ID NO: 1) of Example 1, cell viability of YIGSR peptide-treated cells did not show a significant difference, and a difference in cell viability depending on the treatment does of YIGSR peptide (SEQ ID NO: 1) was not observed either.

In sequence, cell viability depending on a period of time of YIGSR peptide (SEQ ID NO: 1) treatment according to one embodiment of the present invention was analyzed. Hs27 cells of Example 3 were seeded on a 96-well plate at the ratio of 1×$10^4$ cells/well, and then cultured for 24 hours. Thereafter, cells were further cultured for 24 hours in a serum-free medium. Then, cells were treated with YIGSR peptide (SEQ ID NO: 1) of Example 1 in the concentration of $10^3$ nM, and cell viability was analyzed while culturing cells for 0, 0.1, 0.25, 0.5, 1, 3, 6, 12, and 24 hours.

Figure 2B:
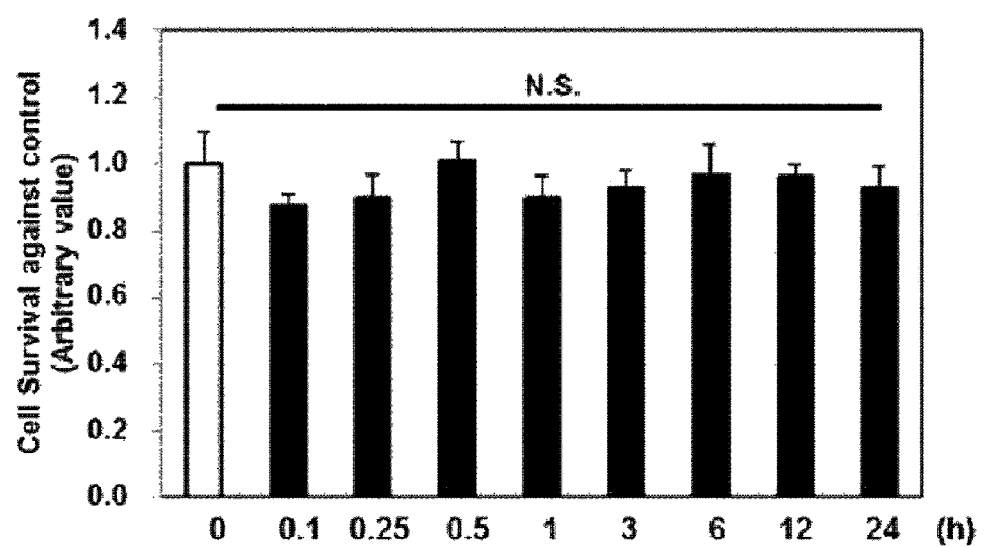

Consequently, as shown in FIG. 2b, when 1 μM of YIGSR peptide (SEQ ID NO: 1) of example 1 was treated and Hs27 cell viability was observed for 24 hours, there was no significant difference from untreated group (see FIG. 2b). The result demonstrates that YIGSR peptide (SEQ ID NO: 1) according to one embodiment of the present invention regulates collagen I expression in a transcriptional level without affecting cell viability.

Experimental Example 3: Analysis of Change in MMP-1 Expression by YIGSR Peptide

MMP-1 is a well known protease which degrades collagen. Therefore, to evaluate whether decrease in MMP-1 expression causes increase in collagen I expression triggered by YIGSR peptide (SEQ ID NO: 1) according to one embodiment of the present invention or not, an expression level of MMP-1 depending on a period of time of YIGSR peptide (SEQ ID NO: 1) treatment was evaluated through western blot analysis. Hs27 cells of Example 3 were cultured and then further cultured for 24 hours in a serum-free medium. Then, cells were treated with $10^3$ nM of YIGSR peptide (SEQ ID NO: 1) of Example 1, and cultured for 0, 0.1, 0.25, 0.5, 1, 3, 6, 12, and 24 hours. Then, western-blot was performed on the cell under the same condition as described in Experimental Example 1 by using MMP-1 (R&D systems, USA) as a primary antibody. In addition, amounts of expression were quantitatively compared by using image J program (Ver 1.38, //rsbweb.nih.gov/ij/index.html) for the western blot image.

Figure 3:
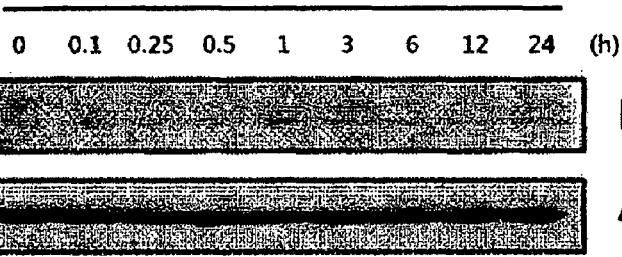
FIG. 3 is an image of evaluating a change in MMP-1 hydrolase expression by YIGSR peptide (SEQ ID NO: 1) treatment according to one embodiment of the present invention through western blot analysis.
Figure 3:
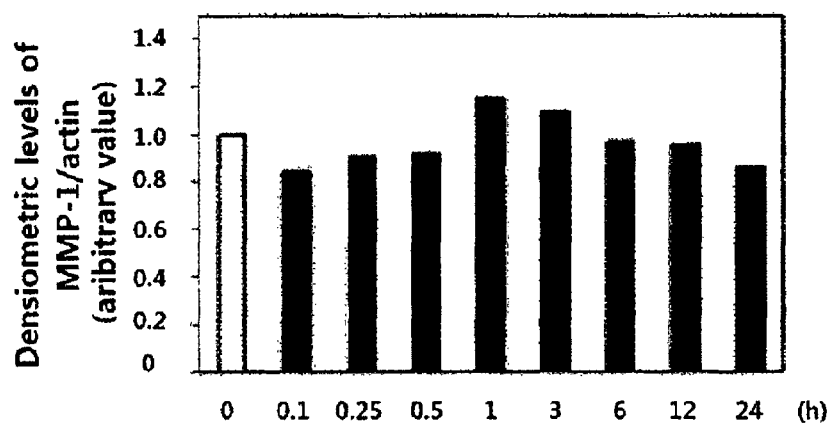

Consequently, as shown in FIG. 3, there was no observed significant difference in expression levels of MMP-1 protein depending on a period of treatment time of YIGSR peptide (SEQ ID NO: 1) (see FIG. 3).

The result demonstrates that increase in collagen expression in cells due to treatment of YIGSR peptide (SEQ ID NO: 1) according to one embodiment of the present invention is not resulted from decrease in MMP-1 expression, but activation of a signal transduction process which enhances expression of collagen I gene.

Experimental Example 4: Analysis of Change in Phosphorylation Levels of FAK, Pyk2 and ERK by YIGSR Peptide To verify a signal transduction process which regulates collagen I expression, the present inventors focused on a downstream signal transduction mechanism of a laminin receptor. YIGSR peptide (SEQ ID NO: 1) has been known to bind to the laminin receptor and to transduce a cellular signal. As an example of such cellular signal transduction, phosphorylation of FAK and Pyk2 has been known. A tyrosine kinase, FAK has been known to involve in cellular adhesion and spreading process (see J. T. Parsons et al., *Oncogene*, 19: 5606-5613, 2000). It has been known that FAK involve in focal adhesion between cells, and plays an important role in cell migration and survival (See J. L. Guan et al., *Nature,* 358: 690-692, 1992). It has been known that Pyk2 plays an important role in cell spreading and migration through a signaling mechanism of G-protein coupled receptor and MAP kinase (see H. Tang et al., *J. Biol. Chem.,* 277: 5441-5447, 2002). Therefore, the present inventors observed phosphorylation levels of FAK, pyK2, and ERK depending on a period of treatment time of YIGSR peptide (SEQ ID NO: 1). Western blot analysis was performed under the same condition as Experimental Example 1 by using FAK (Cell signaling, USA) phospho-FAK (Tyr397, Cell signaling, USA), pyk2 (Cell signaling, USA), phospho-pyk2 (Tyr402, Cell signaling, USA), ERK (Santa Cruz Biotechnology, USA), and phospho-ERK (Thr202/Tyr204, Abcam, USA) as a primary antibody.

Figure 4B:
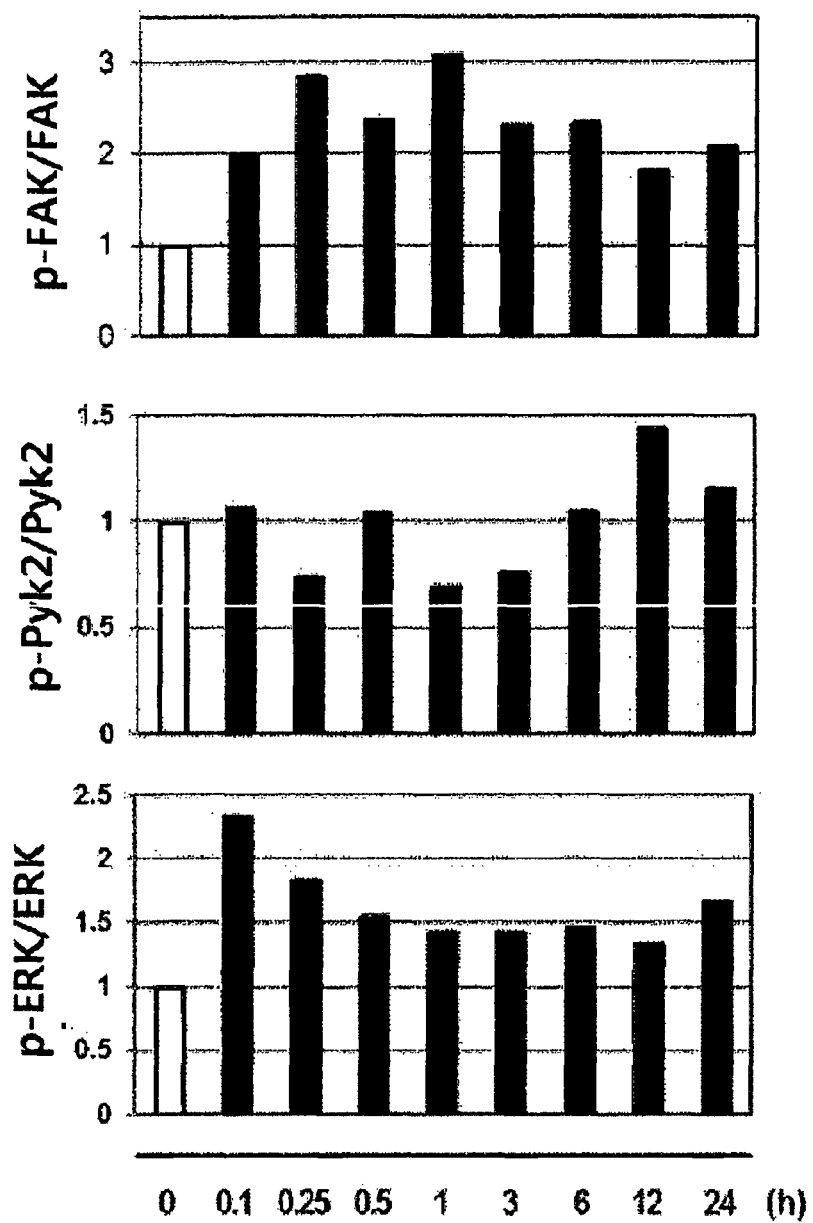

Consequently, as shown in FIG. 4a, there was a tendency, in which phosphorylation of FAK (Tyr397) was remarkably increased according to a period of treatment time of YIGSR peptide (SEQ ID NO: 1). The phosphorylation level of FAK was started to increase at 0.1 hours (6 minutes) and phosphorylation was continued for 24 hours. In addition, when the protein expression levels were quantitatively compared through densitometric analysis, the phosphorylation level was increased by about 2 times of untreatment due to YIGSR peptide (SEQ ID NO: 1) treatment, and remained for 24 hours after treatment (See FIG. 4b).

Further, increase in phosphorylation of Pyk2 (Tyr402) was observed at 6 hours after treatment, which is late than phosphorylation of FAK, and a comparison through densitometric analysis showed that phosphorylation for 12 hour treatment was increased by about 1.5 times of untreatment (see FIGS. 4a and 4b).

In addition, for MAPK/ERK, a phosphorylation level was rapidly increased as soon as YIGSR peptide (SEQ ID NO: 1) treatment by about 2.5 times than that of untreatment, and such increase in phosphorylation was continued until 24 hours (see FIGS. 4a and 4b).

The result demonstrates that YIGSR peptide (SEQ ID NO: 1) according to one embodiment of the present invention induces phosphorylation of the laminin receptor through downstream signal transduction mechanism including FAK, Pyk2, and ERK in Hs27 human fibroblasts.

Experimental Example 5: Analysis of Change in YIGSR Peptide-Inducing Collagen I Expression by FAK and MEK Inhibitors To evaluate whether collagen I expression induced by YIGSR peptide according to one embodiment of the present invention is mediated by FAK and MAPK or not, FAK and MEK inhibitors were used.

Hs27 cells of Example 3 were cultured in a 24-well plate provided that the cells were cultured in a serum-free state for 24 hours. Then, the cells were treated with 1 µM of the FAK-specific inhibitor, PF573228 (Tocris Bioscience, United Kingdom) for 24 hours. To evaluate whether collagen I expression induced by YIGSR peptide (SEQ ID NO: 1) according to one embodiment of the present invention is mediated by FAK or not, cells were treated together with or without 1 µM YIGSR peptide (SEQ ID NO: 1), and collagen I expression was analyzed through western blot analysis.

Figure 5A:
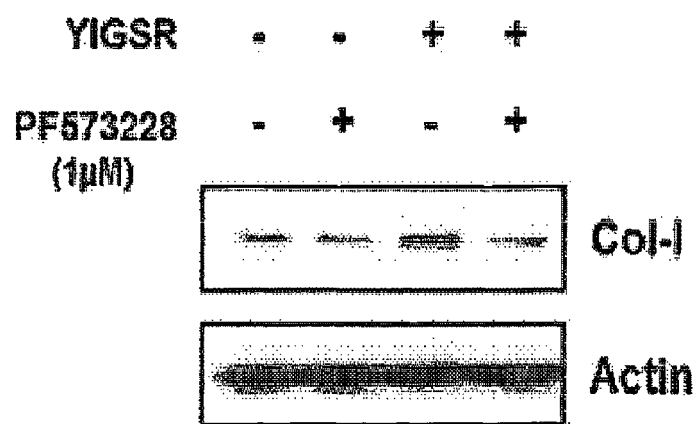
FIGS. 5a and 5b are western blot analysis images showing that collagen production, which is induced by YIGSR peptide (SEQ ID NO: 1) according to one embodiment of the present invention, is inhibited by FAK or ERK inhibitor treatment.

Consequently, as shown in FIG. 5a, when PF573228, which is an FAK inhibitor, was treated, collagen I expression induced by YIGSR peptide (SEQ ID NO: 1) was remarkably repressed. The result demonstrates that collagen I expression induced by YIGSR peptide (SEQ ID NO: 1) is mediated by FAK activation (see FIG. 5a).

In addition, to evaluate whether MAPK/ERK signaling mechanism involves in collagen I expression induced by YIGSR peptide (SEQ ID NO: 1), Hs27 cells were treated with YIGSR peptide (SEQ ID NO: 1) and PD98059 (Tocris Bioscience, United Kingdom), which is a MAPK/ERK-specific inhibitor, and an experiment was performed under the same condition as in the FAK inhibitor treatment experiment.

Figure 5B:
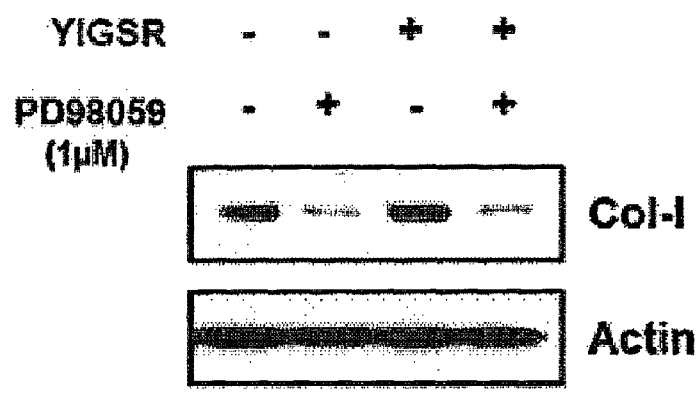

Consequently, as shown in FIG. 5b, expression of collagen I induced by YIGSR peptide (SEQ ID NO: 1) was remarkably inhibited when MEK inhibitor PD98059 was treated (See FIG. 5b). Namely, the result demonstrates that collagen I expression induced by YIGSR peptide (SEQ ID NO: 1) is mediated by MAPK/ERK signal mechanism (see FIG. 5b).

Experimental Example 6: Analysis of Collagen Synthesis and ERK Phosphorylation by Pal-YIGSR Peptide Hs27 skin fibroblasts, which are under culture, were treated with the peptide derivatives prepared in Examples 1 and 2, and Comparative Example 2, and an amount of expressed type I collagen in the cells were measured by an immunoblotting method. The Hs27 skin fibroblasts were cultured by using DMEM medium, (Lonza, USA), to which 10% FBS was added (Lonza, USA), under the condition of 95% of humidity, 5% $CO_2$, and 37° C. Hs27 skin fibroblasts were treated with each concentration of the peptide (0, 2, 25, 50 and 100 µM) for 24 hours or 100 µM of the peptide for each period of time (0, 0.5, 6, 12 and 24 hours). Then, the treated cells were sonicated in the lysis buffer (150 mM NaCl, 1% Triton X-100, 10 mM Tris, 1 mM EDTA, pH 7.4). Thereafter, supernatant was isolated through centrifugation, and quantification was performed through Bradford assay. The same amount of a protein was mixed in a 5× sample buffer and the mixture was heated for 5 minutes at 95° C. The resultant was electrophoresed on 6-15% concentration gradient SDS-Polyacrylamide gel electrophoresis (SDS-PAGE) and then adsorbed to a nitrocellulose membrane. Anti-type I collagen primary antibody (Rockland, USA), anti-phospho-ERK primary antibody (Cell signaling, USA), and anti-actin primary antibody (Santa Cruz, USA) were diluted in TBST buffer (Tris buffered saline with 0.05% Tween 20, pH 7.6) including 5% skimmed milk and reacted for 16 hours. Then, the resultant was washed with TBST for 10 minutes 6 times. Then, the membrane was treated with anti-mouse rabbit peroxidase-conjugated secondary antibody (KPL, USA) for reaction for one hour at room temperature, and washed again with TBST 6 times for 10 minutes followed by development with the enhanced chemiluminescent (ECL) solution (Amersham, USA) for evaluation.

Figure 6A:
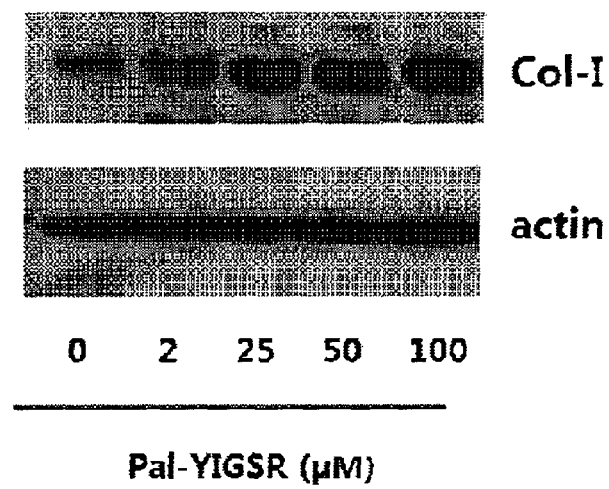
FIGS. 6a and 6b show immunoblotting analysis results showing a concentration-dependent collagen-synthesizing activity of the N-terminally palmitoylated YIGSR peptide (Pal-YIGSR) (Pal-SEQ ID NO: 1) according to the present invention.
Figure 6B:
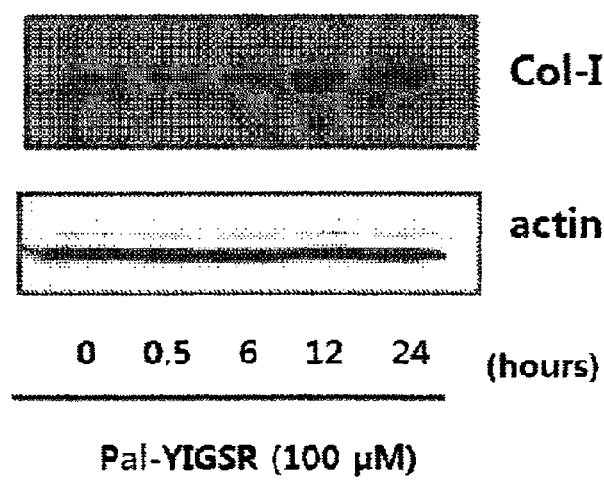
Figure 7:
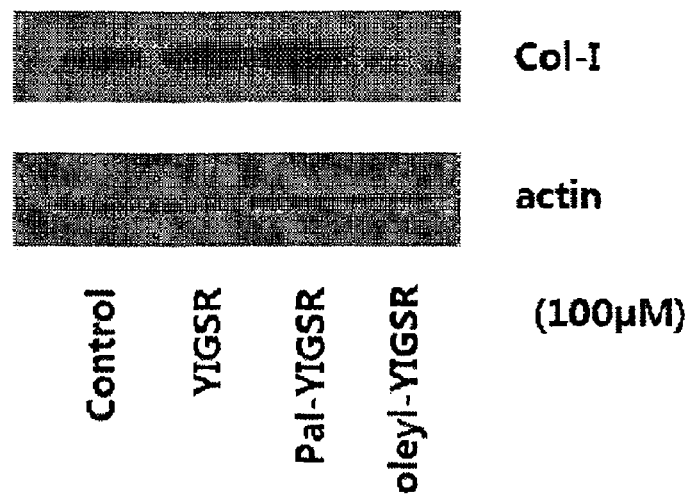
FIG. 7 shows an immunoblotting analysis result comparing a collagen-synthesizing activity of the N-terminally palmitoylated YIGSR peptide (Pal-YIGSR) (Pal-SEQ ID NO: 1) according to the present invention with that of a Comparative Example.

Consequently, it appeared an influence of Pal-YIGSR on collagen synthesis in skin fibroblasts is that an amount of synthesized collagen was increased as concentration increased, and also an amount of synthesized collagen was increased as exposure time increased (FIG. 6). YIGSR (SEQ ID NO: 1) also increased collagen synthesis, although the degree of synthesis is lower than that of Pal-YIGSR (Pal-SEQ ID NO: 1). However, oleyl-YIGSR (oleyl-SEQ ID NO: 1) showed no difference from the control in degrees of collagen synthesis (FIG. 7).

Figure 8:
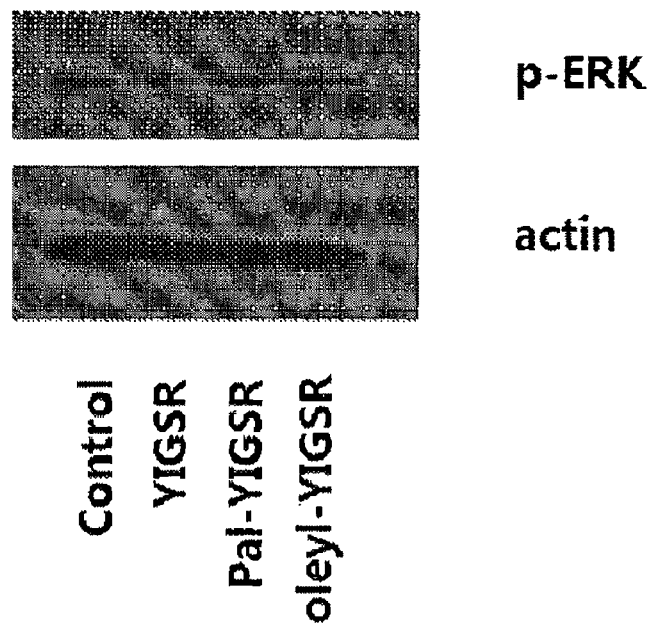
FIG. 8 shows an immunoblotting analysis result comparing an Erk phosphorylation activity of the N-terminally palmitoylated YIGSR peptide (Pal-YIGSR) (Pal-SEQ ID NO: 1) according to the present invention with that of the peptide of the Comparative Example.

Moreover, ERK phosphorylation induction by Pal-YIGSR (Pal-SEQ ID NO: 1) was also observed in skin fibroblasts (FIG. 8). However, YIGSR (SEQ ID NO: 1) and oleyl-YIGSR (oleyl-SEQ ID NO: 1) rarely affect ERK phosphorylation.

Experimental Example 7: Analysis of Influence of Palmitoyl Group

To evaluate whether increase in collagen synthesis by Pal-YIGSR (Pal-SEQ ID NO: 1) is solely affected by a palmitoyl group, the present inventors performed an experiment by using RGD peptide having a known cell-adhering ability.

Specifically, the experiment same as Experimental Example 1 was performed by using Pal-RGD peptide prepared in Comparative Example 1 and RGD peptide to which a palmitoyl group is not attached.

Figure 10:
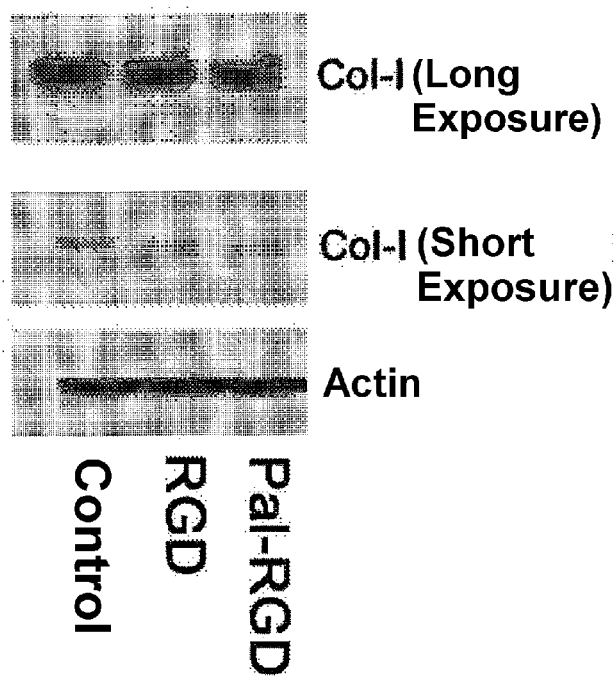
FIG. 10 shows an immunoblotting analysis result comparing a collagen-synthesizing activity of the N-terminally palmitoylated YIGSR peptide (Pal-YIGSR) (Pal-SEQ ID NO: 1) according to the present invention with that of the peptide of Comparative Example depending on exposure time.

Consequently, collagen synthesis degrees of both RGD peptide and Pal-RGD peptide were not significantly different from that of the control (FIG. 10). The result suggests that increase in collagen synthesis by the peptide derivative of the present invention is not simply derived from a function of palmitoyl group per se.

Experimental Example 8: Measurement of Cell Growth by Pal-YIGSR Peptide

The Hs27 skin fibroblasts were seeded on a 24-well culture plate (40,000 cells per each), and cultured under 5% $CO_2$, and 37° C. for 24 hours to allow cells to be attached to a bottom of the culture plate. Next day, a medium was changed to a medium including FBS. Then, cells were cultured again for 24 hours and treated with the peptide derivatives of Examples 1 and 2, and Comparative Examples 1 and 2 followed by further culture of 72 hours. Then, cell growth was measured through crystal violet assay.

Specifically, the medium in each well was removed, and 500 ml of 0.1% crystal violet solution was added to each well followed by 5 minutes of staining. Then, the crystal violet solution was removed, and wells were washed with deionized water four times until the well became transparent. When the washed distilled water became transparent, distilled water was removed. Then, 1 ml of 95% ethanol was added with stirring for 20 minutes to dissolve crystal violet from stained cells. 200 ml of the solution was dispensed to a 96-well plate, and absorbance was measured at 590 nm by using ELISA reader. Then, relative cell growth was calculated by using, as a control, a group which was not treated with a material to be tested.

Figure 9:
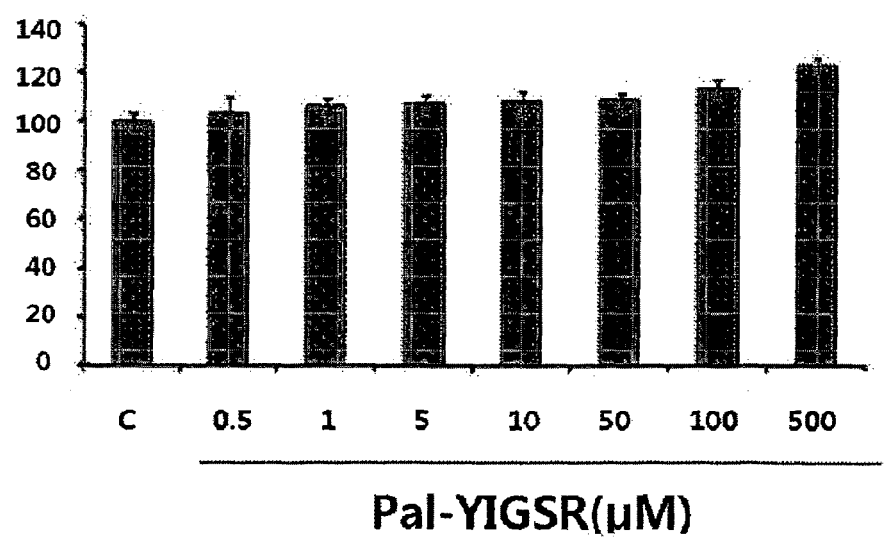
FIG. 9 is a graph showing an activity of the N-terminally palmitoylated YIGSR peptide (Pal-YIGSR) (Pal-SEQ ID NO: 1) according to the present invention to proliferate skin fibroblasts in a concentration-dependent manner.

Consequently, Pal-YIGSR (Pal-SEQ ID NO: 1) showed cell growth in a concentration ranging from 0.5-50 μM, and particularly 13% and 23% of cell growth were respectively shown in concentrations of 100 and 500 μM (FIG. 9).

As described above, the Pal-YIGSR peptide (Pal-SEQ ID NO: 1) derivative according to one embodiment of the present invention increases type I collagen production in cultured skin fibroblasts and facilitates growth of fibroblasts, which demonstrates that the peptide derivative of the present invention can be used as an active material in future development of antiaging and wound repair agents.

Preparation Example

Preparation Example 1: Injection Agent

An injection agent containing 10 mg of a YIGSR peptide (SEQ ID NO: 1) derivative was prepared by the method as follows.

10 mg of the YIGSR peptide (SEQ ID NO: 1) derivative and 0.6 g of sodium chloride were dissolved in purified water (q.s. to 100 ml). The solution was filtered with a 0.2 μm filter for sterilization.

Ingredients of the injection agent are as below.

| Ingredient | Content (wt %) |
| --- | --- |
| Purified water | To 100 |
| YIGSR peptide (SEQ ID NO: 1) | 0.01 |
| Sodium chloride | 0.6 |

Preparation Example 2: Toner (Skin Lotion)

A toner containing YIGSR peptide (SEQ ID NO: 1) as below was prepared by a typical method of preparing a toner.

| Ingredient | Content (wt %) |
| --- | --- |
| Purified water | To 100 |
| YIGSR peptide (SEQ ID NO: 1) | 0.01 |
| Butylene glycol | 2.0 |
| Propylene glycol | 2.0 |
| Carboxyvinyl polymer | 0.1 |
| PEG-12 Nonylphenyl ether | 0.2 |
| Polysorbate 80 | 0.4 |
| Ethanol | 10.0 |
| Triethanol amine | 0.1 |
| Preservant, pigment, flavoring agent | Suitable amount |

Preparation Example 3: Nourishing Softener (Milk Lotion)

A nourishing softener containing YIGSR peptide (SEQ ID NO: 1) as below was prepared by a typical method of preparing a nourishing softener.

| Ingredient | Content (wt %) |
| --- | --- |
| Purified water | To 100 |
| YIGSR peptide (SEQ ID NO: 1) | 0.01 |
| Bee wax | 4.0 |
| Polysorbate 60 | 1.5 |
| Sorbitan sesquioleate | 1.5 |
| Liquid paraffin | 0.5 |
| Caprylic/Capric Triglyceride | 5.0 |
| Glycerin | 3.0 |
| Butylene glycol | 3.0 |
| Propylene glycol | 3.0 |
| Carboxyvinyl polymer | 0.1 |
| Triethanol amine | 0.2 |
| Preservant, pigment, flavoring agent | Suitable amount |

Preparation Example 4: Nourishing Cream

A nourishing cream containing YIGSR peptide (SEQ ID NO: 1) as below was prepared by a typical method of preparing a nourishing cream.

| Ingredient | Content (wt %) |
| --- | --- |
| Purified water | To 100 |
| YIGSR peptide (SEQ ID NO: 1) | 0.01 |
| Bee wax | 10.0 |

-continued

| Ingredient | Content (wt %) |
| --- | --- |
| Polysorbate 60 | 1.5 |
| PEG 60 harden castor oil | 2.0 |
| Sorbitan sesquioleate | 0.5 |
| Liquid paraffin | 10.0 |
| Squalane | 5.0 |
| Caprylic/capric triglyceride | 5.0 |
| Glycerin | 5.0 |
| Butylene glycol | 3.0 |
| Propylene glycol | 3.0 |
| Triethanol amine | 0.2 |
| Preservant, pigment, flavoring agent | Suitable amount |

Preparation Example 5: Massage Cream

A massage cream containing YIGSR peptide (SEQ ID NO: 1) as below was prepared by a typical method of preparing a massage cream.

| Ingredient | Content (wt %) |
| --- | --- |
| Purified water | To 100 |
| YIGSR peptide (SEQ ID NO: 1) | 0.01 |
| Bee wax | 10.0 |
| Polysorbate 60 | 1.5 |
| PEG 60 hardened castor oil | 2.0 |
| Sorbitan sesquioleate | 0.8 |
| Liquid paraffin | 40.0 |
| Squalane | 5.0 |
| Caprylic/capric triglyceride | 4.0 |
| Glycerin | 5.0 |
| Butylene glycol | 3.0 |
| Propylene glycol | 3.0 |
| Triethanol amine | 0.2 |
| Preservant, pigment, flavoring agent | Suitable amount |

Preparation Example 6: Pack

A pack containing YIGSR peptide as below was prepared by a typical method of preparing a pack.

| Ingredient | content (wt %) |
| --- | --- |
| Purified water | To 100 |
| YIGSR peptide (SEQ ID NO: 1) | 0.01 |
| Polyvinyl alcohol | 13.0 |
| Sodium carboxymethyl cellulose | 0.2 |
| Glycerin | 5.0 |
| Allantoin | 0.1 |
| Ethanol | 6.0 |
| PEG-12 nonylphenyl ether | 0.3 |
| Polysorbate 60 | 0.3 |
| Preservant, pigment, flavoring agent | Suitable amount |

Preparation Example 7: Dermal Filler

A dermal filler containing YIGSR peptide (SEQ ID NO: 1) as below was prepared by a typical method of preparing a dermal filler.

| Ingredient | Content (wt %) |
| --- | --- |
| Purified water | To 100 |
| YIGSR peptide (SEQ ID NO: 1) | 0.01 |
| Human collagen | 3.5 |
| Potassium chloride (KCl) | 0.02 |
| Monopotassium phosphate ($KH_2PO_4$) | 0.024 |
| Sodium chloride (NaCl) | 0.8 |
| Sodium Phosphate, Dibasic ($Na_2HPO_4$) | 0.1145 |
| Preservant | Suitable amount |

Although the present invention has been described with reference to the Examples, Experimental Examples and Preparation Examples above, it will be understood that the Examples, Experimental Examples and Preparation Examples are for illustrative, and numerous modifications and other equivalent examples may be derived by a person skilled in the art. Therefore, the technical protection scope of the present invention should be defined based on the technical spirit of the accompanying claims.

It has been demonstrated that YIGSR Peptide (SEQ ID NO: 1) according to one embodiment of the present invention can induce collagen production by identifying that the peptide can increase collagen I production in a transcriptional level without affecting cell viability, and does not reduce expression of MMP-1 protein hydrolase which degrades collagen I protein. Thus, YIGSR peptide (SEQ ID NO: 1) according to one embodiment of the present invention can be useful as a cosmetic composition for alleviating wrinkle and skin aging and pharmaceutical composition for wound healing which may be triggered by reduction of collagen.

BRIEF DESCRIPTION OF THE SEQUENCE LISTING

SEQ ID NO: 1 indicates a sequence having a collagen-synthesizing ability according to one embodiment of the present invention.

SEQ ID NO: 2 indicates a sense primer for collagen I mRNA amplification.

SEQ ID NO: 3 indicates an anti-sense primer for collagen I mRNA amplification.

The invention claimed is:

1. A method of alleviating a wrinkle of a subject comprising: administering a pharmaceutically effective amount of YIGSR peptide consisting of the amino acid sequence of SEQ ID NO: 1 or the palmitoylated peptide of said YIGSR peptide (SEQ ID NO: 1) in which a palmitoyl group is added to an N-terminal of said YIGSR peptide (SEQ ID NO:1) dermally to the subject.

* * * * *

SEQUENCE LISTING

```
<160> NUMBER OF SEQ ID NOS: 3

<210> SEQ ID NO 1
<211> LENGTH: 5
<212> TYPE: PRT
<213> ORGANISM: Artificial
<220> FEATURE:
<223> OTHER INFORMATION: YIGSR petide
```

```
<400> SEQUENCE: 1

Tyr Ile Gly Ser Arg
 1               5

<210> SEQ ID NO 2
<211> LENGTH: 20
<212> TYPE: DNA
<213> ORGANISM: Artificial
<220> FEATURE:
<223> OTHER INFORMATION: Forward primer for Collagen I

<400> SEQUENCE: 2
gaacgcgtgt catcccttgt                                              20

<210> SEQ ID NO 3
<211> LENGTH: 24
<212> TYPE: DNA
<213> ORGANISM: Artificial
<220> FEATURE:
<223> OTHER INFORMATION: Reward primer for Collagen I

<400> SEQUENCE: 3
gaacgaggta gtctttcagc aaca                                         24
```